United States Patent
Galloway et al.

(10) Patent No.: US 10,780,591 B2
(45) Date of Patent: Sep. 22, 2020

(54) SOFT ROBOTIC ACTUATORS AND GRIPPERS

(71) Applicant: President and Fellows of Harvard College, Cambridge, MA (US)

(72) Inventors: Kevin C. Galloway, Somerville, MA (US); Robert J. Wood, Cambridge, MA (US); Kaitlyn Becker, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/070,861

(22) PCT Filed: Jan. 19, 2017

(86) PCT No.: PCT/US2017/014054
§ 371 (c)(1),
(2) Date: Jul. 18, 2018

(87) PCT Pub. No.: WO2017/127497
PCT Pub. Date: Jul. 27, 2017

(65) Prior Publication Data
US 2019/0022875 A1    Jan. 24, 2019

Related U.S. Application Data

(60) Provisional application No. 62/280,401, filed on Jan. 19, 2016.

(51) Int. Cl.
*B25J 15/12* (2006.01)
*A61B 34/30* (2016.01)
(Continued)

(52) U.S. Cl.
CPC .............. *B25J 15/12* (2013.01); *A61B 34/30* (2016.02); *B25J 15/0023* (2013.01); *B25J 15/0066* (2013.01); *B25J 15/0475* (2013.01); *B25J 15/10* (2013.01); *B29C 33/46* (2013.01); *B29C 33/76* (2013.01); *B29L 2031/703* (2013.01)

(58) Field of Classification Search
CPC ......... B29C 45/43; B29C 33/46; B29C 33/76; A47L 9/2836; A61B 1/008; A61B 34/30;
(Continued)

(56) References Cited

U.S. PATENT DOCUMENTS 3,343,864 A * 9/1967 Baer .................... B25J 15/0009
294/119.3
3,640,564 A * 2/1972 Kuster ................... B25B 11/00
294/119.3
(Continued)

FOREIGN PATENT DOCUMENTS

JP    S61-262112 A    11/1986

OTHER PUBLICATIONS

International Search Report and Written Opinion dated May 19, 2017, in the International Application No. PCT/US2017/014054, filed Jan. 19, 2017, 16 pages.
(Continued)

*Primary Examiner* — Stephen A Vu
(74) *Attorney, Agent, or Firm* — Wilmer Cutler Pickering Hale and Dorr LLP

(57) ABSTRACT

A method of making an actuator having a complex internal shape includes providing a core of a shape that defines an internal cavity of an actuator; molding an actuator around the core, wherein the core occupies the internal cavity of the actuator, the cavity having an opening; generating a pressure differential between an exterior surface of the actuator and the internal cavity of the actuator, wherein the external pressure is less than the internal pressure, to expand the actuator cavity; and removing the core through the opening of the expanded actuator cavity.

27 Claims, 18 Drawing Sheets

(51) Int. Cl.
  *B25J 15/00* (2006.01)
  *B25J 15/04* (2006.01)
  *B25J 15/10* (2006.01)
  *B29C 33/46* (2006.01)
  *B29C 33/76* (2006.01)
  *B29L 31/00* (2006.01)

(58) Field of Classification Search
  CPC ... B25J 9/142; B25J 18/06; B25J 15/12; B25J 15/0023; B25J 15/0066; B25J 15/0475; B25J 15/10; F15B 15/103; B29L 2031/703
  See application file for complete search history.

(56) References Cited

U.S. PATENT DOCUMENTS

| | | | |
|---|---|---|---|
| 3,776,683 A | | 12/1973 | Putzer et al. |
| 3,935,358 A | | 1/1976 | Wyeth et al. |
| 3,981,528 A | * | 9/1976 | Andorf ............... B25J 15/0023 294/119.3 |
| 5,683,644 A | | 11/1997 | Peterson |
| 6,484,601 B1 | * | 11/2002 | Arrichiello ............... B25J 9/14 294/106 |
| 2003/0110938 A1 | * | 6/2003 | Seto ...................... B25J 9/142 92/92 |
| 2010/0178182 A1 | | 7/2010 | Simmons et al. |
| 2012/0216672 A1 | | 8/2012 | Menon et al. |
| 2014/0109560 A1 | | 4/2014 | Ilievski et al. |
| 2015/0351936 A1 | | 12/2015 | Mosadegh et al. |
| 2016/0075036 A1 | * | 3/2016 | Lessing ................ B25J 9/142 361/234 |

OTHER PUBLICATIONS

European Search Report dated Aug. 16, 2019, in the European Patent Application No. 17741891.0, 15 pages.
Extended European Search Report dated Nov. 21, 2019, in the European Patent Application No. 17741891.0, 13 pages.

* cited by examiner

820

810

800

FIG 16A
FIG 16C
vacuum
FIG 16B
1 cm
FIG 16D 124 kPa
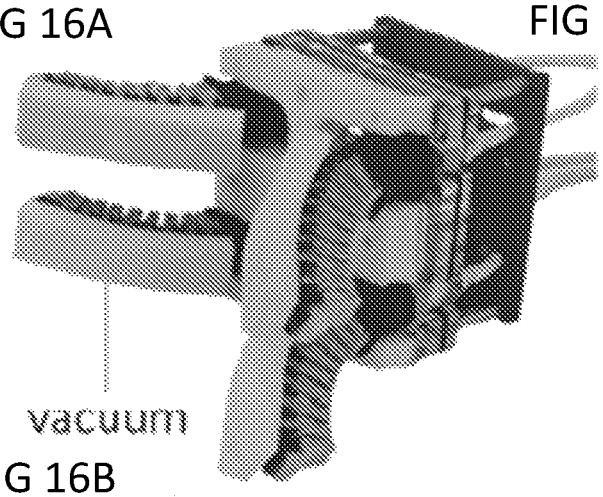
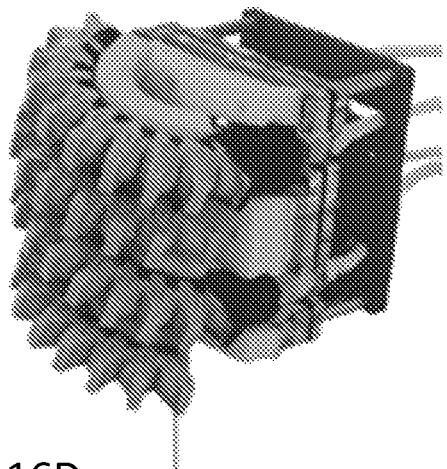
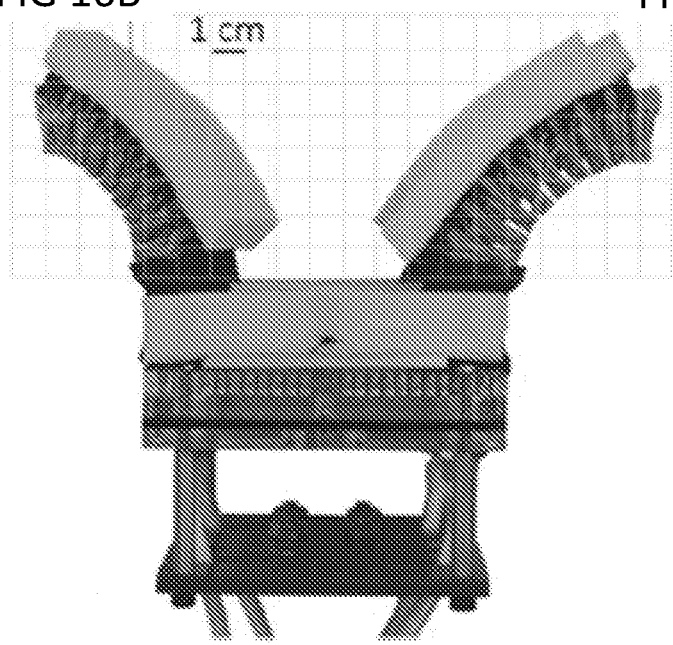
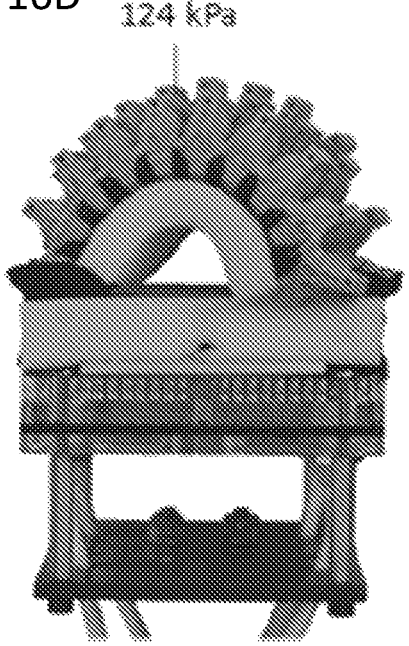

SOFT ROBOTIC ACTUATORS AND GRIPPERS

RELATED APPLICATIONS

This Application is a National Stage Entry of PCT International Application No. PCT/US2017/014054 filed Jan. 19, 2017, which claims priority to U.S. Provisional 62/280,401, filed Jan. 19, 2016, the contents of which are incorporated by reference.

INCORPORATION BY REFERENCE

All patents, patent applications and publications cited herein are hereby incorporated by reference in their entirety to more fully describe the state of the art as known to those skilled therein as of the date of the invention described herein

TECHNICAL FIELD

This technology relates generally to soft robots. In particular, this invention relates to soft robotic actuators and grippers. The technology also relates methods for manufacturing soft robotic actuators and grippers

BACKGROUND

The field of soft robotics has emerged as an alternative to hard-material robotics, providing a safer alternative for robots to interact, in close proximity, with living organisms. By using soft materials instead of more traditional metals and hard polymers, robotic components can closely mimic the properties of natural systems.

Soft robotic grippers are adept at adapting to variations in object size and shape. Furthermore, soft robotic systems are ideally suited for gripping and manipulating delicate objects and complex shapes by conforming to the object's shape and distributing grasping forces. Soft systems also offer improved safety as these pneumatically and hydraulically actuated soft materials are inherently safe for interfacing with humans and animals due to their natural compliance and back drivability.

SUMMARY

This disclosure describes soft robotic grippers and actuators. The soft robotic gripper s and actuators provide a simple construction using inexpensive materials. The modular design of the soft grippers allows one to quickly modify or repair a system in the field with minimal expense and mechanical expertise.

A method of making an actuator having a complex internal shape includes providing a core of a shape that defines an internal cavity of an actuator; molding an actuator around the core, wherein the core occupies the internal cavity of the actuator, the cavity having an opening; generating a pressure differential between an exterior surface of the actuator and the internal cavity of the actuator, wherein the external pressure is less than the internal pressure, to expand the actuator cavity; and removing the core through the opening of the expanded actuator cavity.

In one or more embodiments, the internal cavity is in fluidic communication with the ambient and so that the cavity is open to the exterior of the chamber.

In any preceding embodiment, generating a pressure differential includes fluidically isolating the exterior surface of the actuator from the internal cavity and applying a vacuum to the actuator.

In any preceding embodiment, fluidically isolating the actuator comprises introducing the actuator into a chamber and forming a seal between the cavity opening and the so that the cavity is open to the exterior of the chamber.

In any preceding embodiment, the actuator comprising a flange around the cavity opening and the seal is created between the flange and the chamber.

In any preceding embodiment, the core comprises fins and defines the internal cavity shape of a bellows.

In any preceding embodiment, molding an actuator around the core includes positioning the core in a mold, the mold defining the external shape of a bellows actuator.

In any preceding embodiment, molding the bellows actuator further includes molding thru holes through a tip of the bellows.

In any preceding embodiment, the core is made up of a plurality of branches, and for example, the plurality of branches is in parallel or the plurality of branches are positioned in different directions.

In any preceding embodiment, the actuator is molded around a plurality of cores, each core defining a cavity having an opening.

In any preceding embodiment, the core is a composite core, and optionally the composite core includes a reinforcing member, and for example the reinforcing member is a strain limiting member, a strengthening member or a cantilevered member, a fiber reinforcement, or combinations thereof.

In any preceding embodiment, the fins have a high aspect ratio.

In any preceding embodiment, the method further includes fastening an attachment around the open cavity for use in securing the actuator to a base.

In any preceding embodiment, the method further includes incorporating a valve connection in the open cavity for use in connecting the actuator to a pressurizing source.

In another aspect, a bellows actuator includes a flexible molded body having a flat base and an upper surface molded to define a plurality of fins, each fin secured to the base and at least partially separated from adjacent fins, wherein the fin tips comprise thru holes, said through holes in fluidic isolation from the actuator interior.

In any preceding embodiment, the bellows actuator further includes an attachment secure to the flat base by a string that is thread through the plurality of thru holes.

In any preceding embodiment, the attachment is selected from the group of cushioning material, friction adjusting materials, rigid materials, knitted, woven and non-woven fabrics, and suction cups (active or passive).

In any preceding embodiment, the actuator is closed at one end and open at the opposite end and the open end is fitted with a valve for connection to a pressurizing source.

In any preceding embodiment, the open end further includes gear teeth for meshing with a robot base.

In any preceding embodiment, the flat base includes thru holes, and the through holes in fluidic isolation from the actuator interior.

In other aspect, a soft robotic gripper includes a plurality of bellow actuators according to any of the preceding embodiments, wherein the bellow actuators are secured to a base and positioned to bend towards one another on pressurization.

These and other aspects and embodiments of the disclosure are illustrated and described below.

BRIEF DESCRIPTION OF THE DRAWINGS

The invention is described with reference to the following figures, which are presented for the purpose of illustration only and are not intended to be limiting.

In the Drawings:

FIGS. 16A and 16B provide isometric and top views, respectively, of the bellows-type soft actuators under vacuum in the open pose state.

FIGS. 16C and 16D provide isometric and top views, respectively, of the bellows-type soft actuators pressurized to 124 kPa (18 psi).

DETAILED DESCRIPTION

Figure 1A:
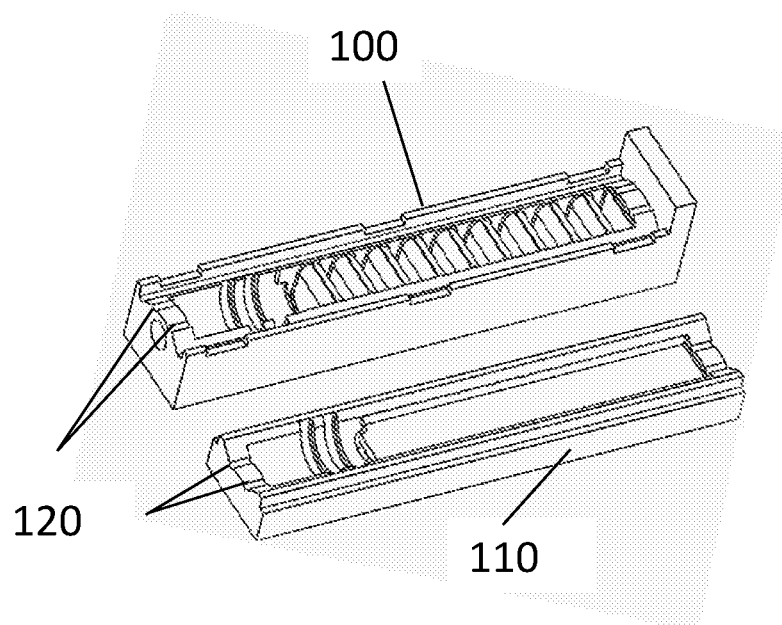
FIG. 1A is a CAD model and FIG. 1B is a photograph of the 3D printed mold used to prepare the core insert, according to one or more embodiments.

Bellows-type soft actuators are a common architecture that creates asymmetric motion by unfolding the excess material in the bellows. Compared to balloon actuators where the elastomer material must strain to create motion, this unfolding approach places less strain on the material, which can increase the longevity of the actuator and reduces the operating pressures. Bellows actuators also have the advantage that certain geometries can support bi-directional bending by alternating pressurized fluid and vacuum. Furthermore, fiber reinforcements can be incorporated into bellows-type actuators to increase the actuator's operating pressure and output force, and reduce its radius of curvature when actuated.

One of the challenging aspects of fabricating a bellows-type soft actuators is molding the inner geometry of the bellows. The high aspect ratio features render any rigid core mechanically constrained and can lead to damage to the core and the actuator body during demolding. Prior methods used a two-step molding technique where one-half of the bellow was molded and then bonded to the other half. However, this introduces a materially weak seam along the actuator's entire perimeter and becomes the source of most actuator failures. Other methods used dissolvable cores to define the inner bellow geometry; however, this is a time consuming process requiring a new core for each new actuator and time spent dissolving the core. In addition, it is difficult to fully remove the dissolvable core from the bellows interior, leaving a contaminating residue.

To overcome these challenges, a new fabrication method is provided that uses reusable 'cores' and a vacuum technique for core removal. The vacuum demolding step offers a technique to apply outward pulling forces on the actuator body by inflating the actuator body using ambient air pressure inside the actuator and vacuum pressure on the outside. While described with reference to the fabrication of bellows-type actuators, the method will benefit and is suitable for use with any molding process for a molded feature having a complex interior shape.

In one or more embodiments, a molded bellows actuator (or other complex expandable geometry) is formed around a reusable core. The core defines the inner shape of the bellows actuator and can include regions of complex interior shape (e.g., fins of a bellow actuator) and less complex surfaces (e.g., a base). The core is removed by generating a pressure differential between the outer surface of soft bellows actuator (at lower pressure) and the inner surface of the soft bellows actuator (at higher pressure), to thereby cause the bellows to expand. Once expanded, the core (which remains at atmospheric pressure and thereby has not undergone a volume change) can be easily removed from the bellows interior. The pressure differential is removed to return the soft bellows actuator to its original size and shape.

The core enables the ability to create complex interior bladder geometries with high-aspect ratios. The vacuum step enables no-damaging (i.e., to the core and the actuator body), core extraction and facilitates core reuse. While this method is particularly useful in creating interior fin features with a high aspect ratio, it is suitable for use with any class of interior features where the core is geometrically locked.

The method is described with reference to FIGS. 1-8.

Figure 1B:
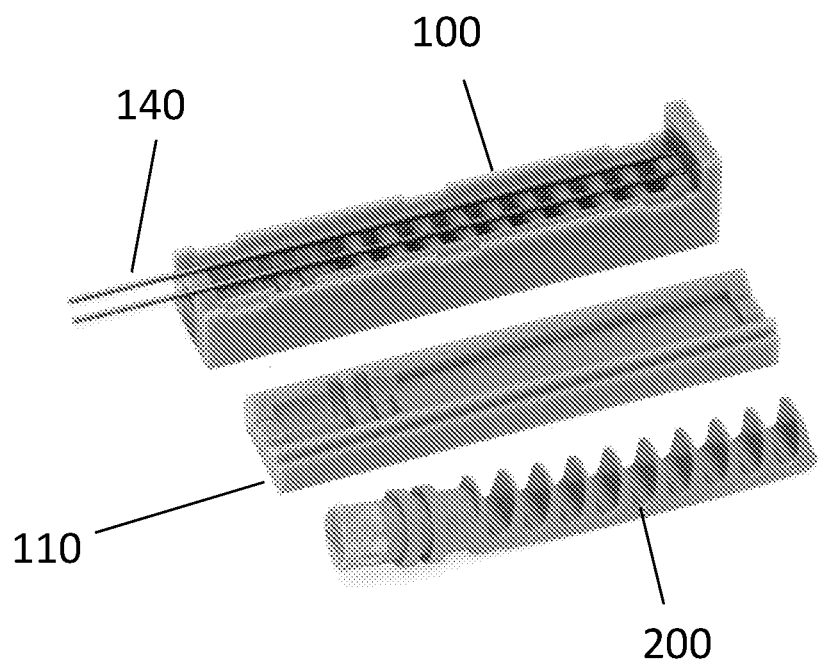
Figure 2:
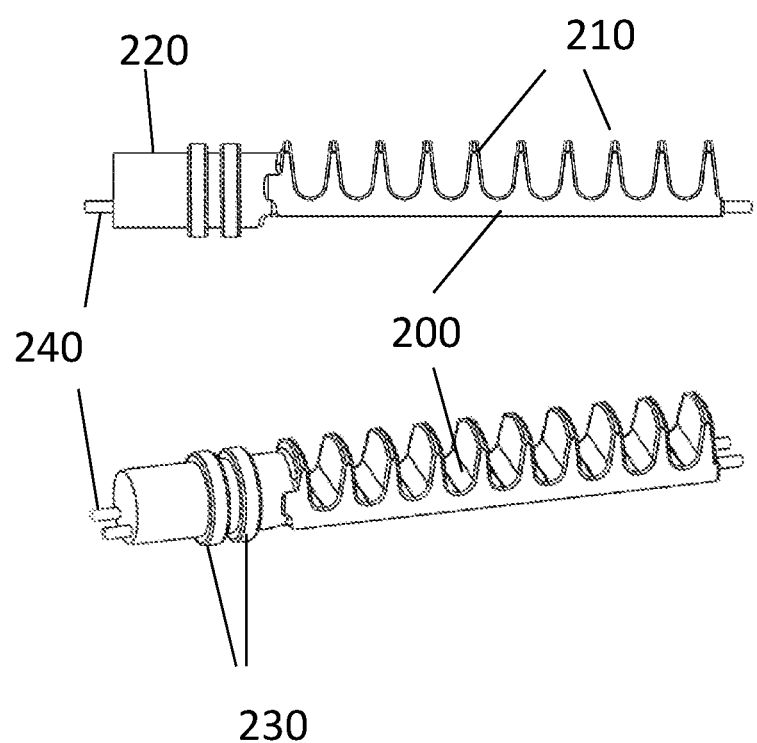
FIG. 2 illustrates the molded core defining the inner bellows geometry in side and perspective view, respectively, according to one or more embodiments.

The first step in fabricating a bellows soft actuator begins with making the core, which will define the bladder geometry of the final actuator. In the present embodiment, the core is molded using 3D printed forms; however, the core can be fabricated by other means such direct 3D printing or machining. FIG. 1A is a CAD model and FIG. 1B is a photograph of the 3D printed mold used to prepare the core insert. The mold includes a base 100 having the bellows features and a top mold 110 having smooth upper surface. The mold further includes alignment features 120 located in both base 100 and top mold 110. The alignment features are used for the placement of reinforcing rods 140, which run the length of the mold and help to prevent sagging or deformation of the molded core. FIG. 1B shows placement of the rods into the mold prior to filling. The two-part mold is filled with a silicone rubber (e.g., M4601 by Wacker Chemical) to form the core 200. Other materials could be used, such as urethane rubbers. During this mold step, two metal rods can also be co-molded with the core, and used to support and align the core in future mold steps. A photograph of the demolded core 200 is shown in FIG. 1B. The core defines the inner bellows geometry and is shown in side and perspective view in FIG. 2. The core 200 includes fins 210 and terminal base 220. Terminal base 220 can include flanges 230 that can serve as sealing gaskets in subsequent operations. The plug with the pneumatic connector has features that match the negative shape of the flanges. This improves the mechanical connection between the actuator rubber and the plug. Stiff inserts 240 are shown protruding from both ends of the core. In other embodiments, the stiff inserts need not extend beyond the body of the core. The mold can include, for example, a cantilever edge along the side of the terminal base, in which case sufficient support is found and no holes need extend beyond the core body. Furthermore, while each fin 210 presented has the same geometrical shape, anyone skilled in the art will recognize, that these protruding features can vary in geometry, orientation and spacing and combined in an infinite number of combinations to yield actuators with unique ranges of motion.

Figure 3A:
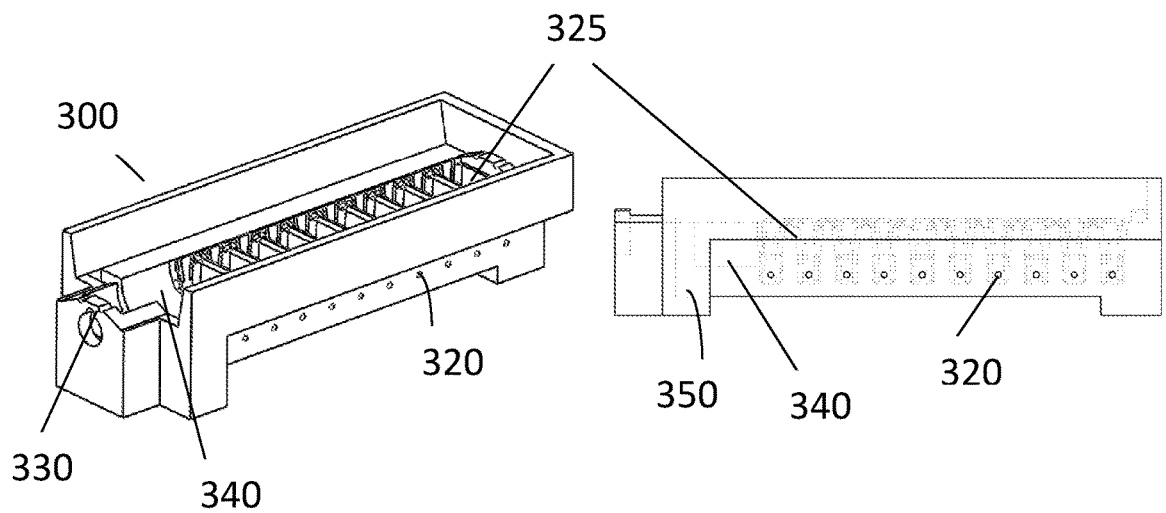
FIGS. 3A and 3B are CAD illustrations of the upper and lower actuator molds, respectively, shown in perspective and side view, according to one or more embodiments.
Figure 3B:
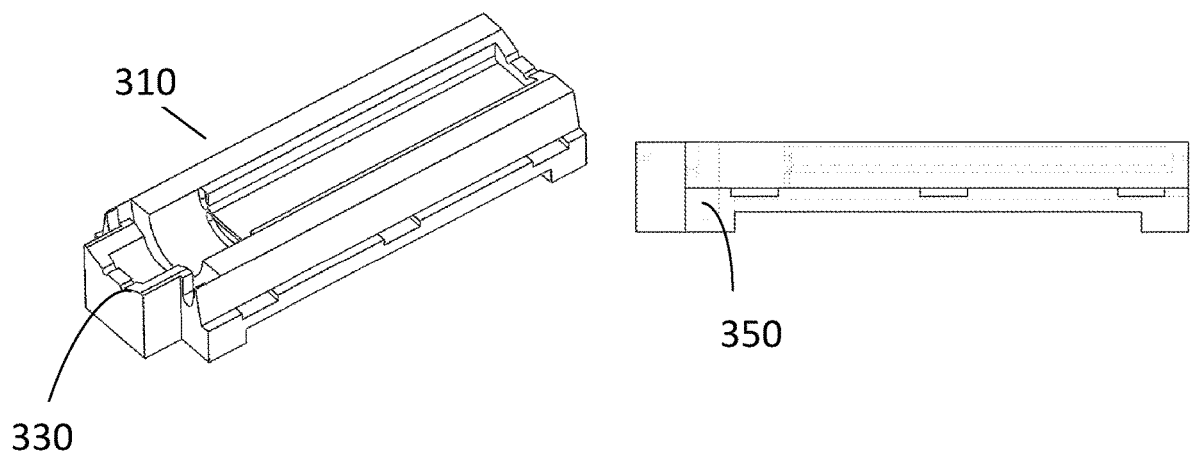

In the second step, a 3D printed mold that defines the outer geometry of the soft actuator is prepared. FIGS. 3A and 3B are CAD illustrations of lower 300 and upper 310 actuator mold parts, respectively, shown in perspective and side view. The lower mold defines the outer surface 325 of the bellows features of the actuator and well or depression 340 that define an edge for attachment of a robot and a lip or flange 350. In some embodiments, lower mold 300 can include holes 320. Pins or rods can be inserted into the holes to create thru holes in the molded actuator. The actuator mold further includes alignment features 330 located in the lower 300 and upper 310 actuator mold parts. The alignment features can receive reinforcing rods (not shown), which run the length of the core and help to prevent sagging or deformation of the molded core.

Figure 4A:
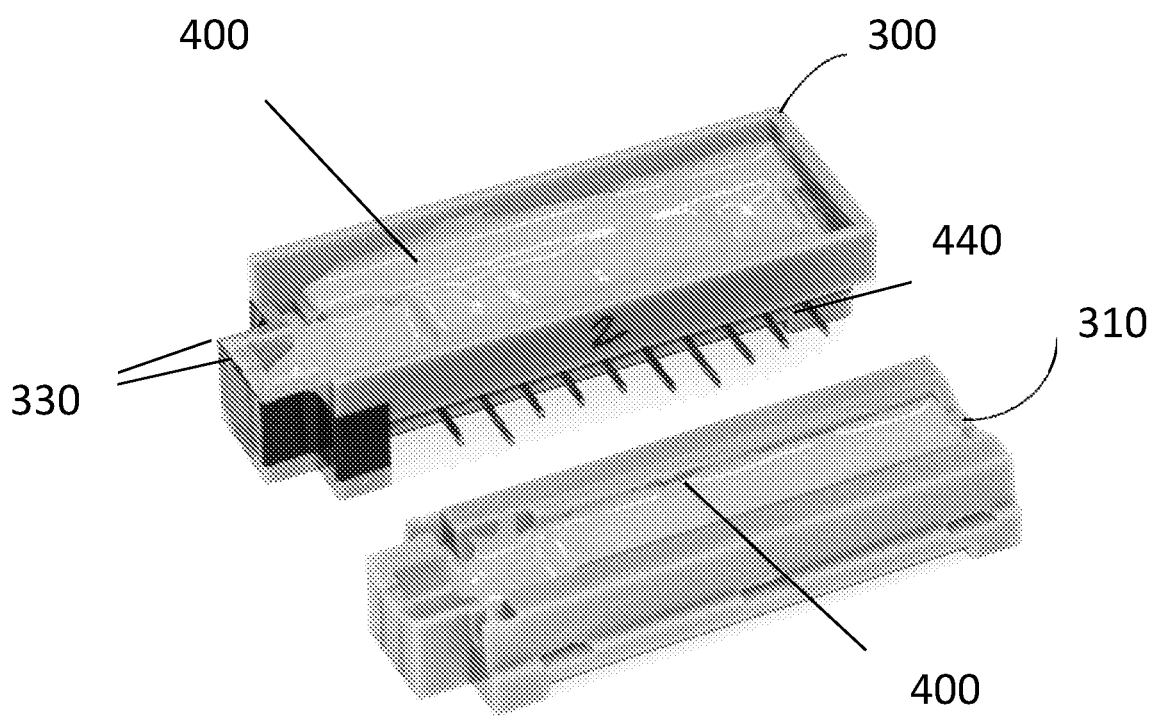
FIG. 4A is a photograph of the upper and lower actuator molds filled with polymer, according to one or more embodiments.

Then the polymer 400 (e.g., Smooth-Sill 950 by Smooth On) for the bellows actuator can be poured into both halves of the mold 300, 310, as shown in FIG. 4A. Anyone skilled in the art will appreciate that the polymer could be injected into the mold rather than poured to facilitate efficient manufacturing and to enable use of rubber compounds that can only be injection molded. In one or more embodiments, the polymer used for the actuator can have a different durometer than the core. By way of example, the core can be made of a silicone of durometer 30A, while the molded actuator can be made of a silicone of durometer 50A. As discussed in greater detail below, the lower the durometer of the core or actuator body makes it easier to remove after the molding process. In this particular mold design, pins 440 are added along the bottom to create through-holes at the top of each bellow. These features serve as anchor points to add reinforcements, bridging materials, and other functions to the actuator.

Figure 4B:
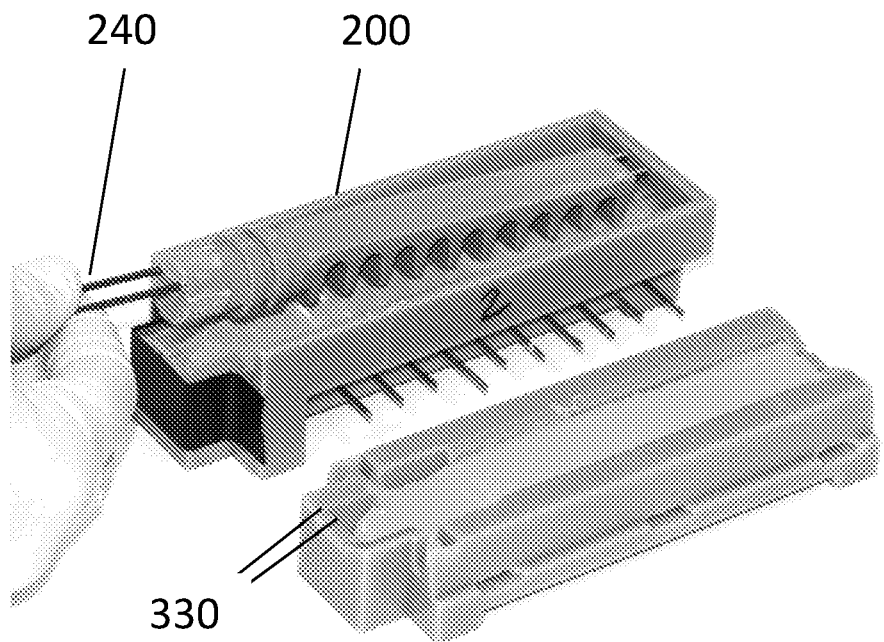
FIG. 4B is a photograph of the core being inserted into the actuator mold, according to one or more embodiments.
Figure 5A:
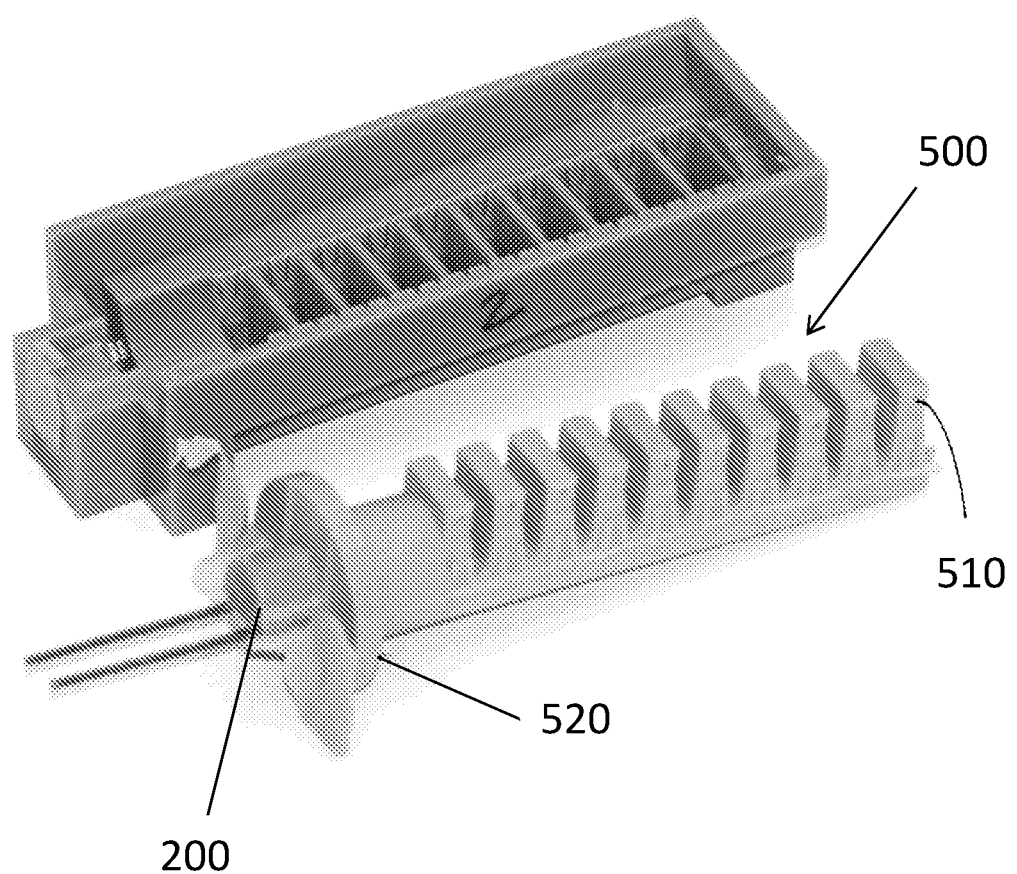
FIG. 5A is a photograph of a demolded actuator with core, according to one or more embodiments.
Figure 5B:
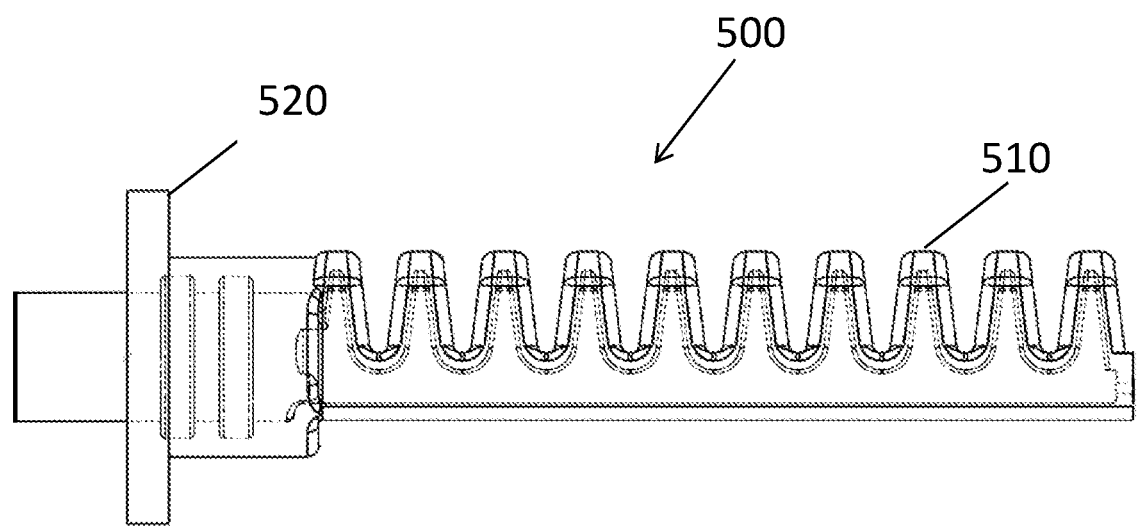
FIG. 5B is a CAD illustration showing the core (dashed lines) surrounded by the soft bellows actuator (solid lines), according to one or more embodiments.

In the fourth step, the core 200 is inserted into the mold, and rods 240 are gently pushed into alignment slots 330 built into the mold, as shown in FIG. 4B. The two halves of the mold are brought together and clamped. Once the polymer has cured, the part can be removed from the mold, as is shown in FIG. 5A. The demolded actuator includes an actuator body 500 having fins 510 and a flange 520. The actuator body 500 is molded around the core 200. FIG. 5B is a CAD illustration showing the core 200 (designated by dashed lines) surrounded by the soft bellows actuator 500 (shown by solid lines). The rods extending beyond the end of the actuator have been removed, which upon removal introduces two small holes at the end of the actuator. These can be plugged with a small amount of glue (e.g., Sil-Poxy by Smooth On). As discussed previously, the holes (and plugging step) can be avoided by cantilevering rods from one end of the mold to create an actuator with a closed end. Furthermore, while the wall thickness of the actuator body is relatively consistent, anyone skilled the art will recognize that the wall thickness can be varied as in the example of creating thru-holes, but also to promote motion of the actuator in one area over another. For example, the wall thickness of select fins may be thinner than others to promote motion at the thinner fins first.

Figure 6:
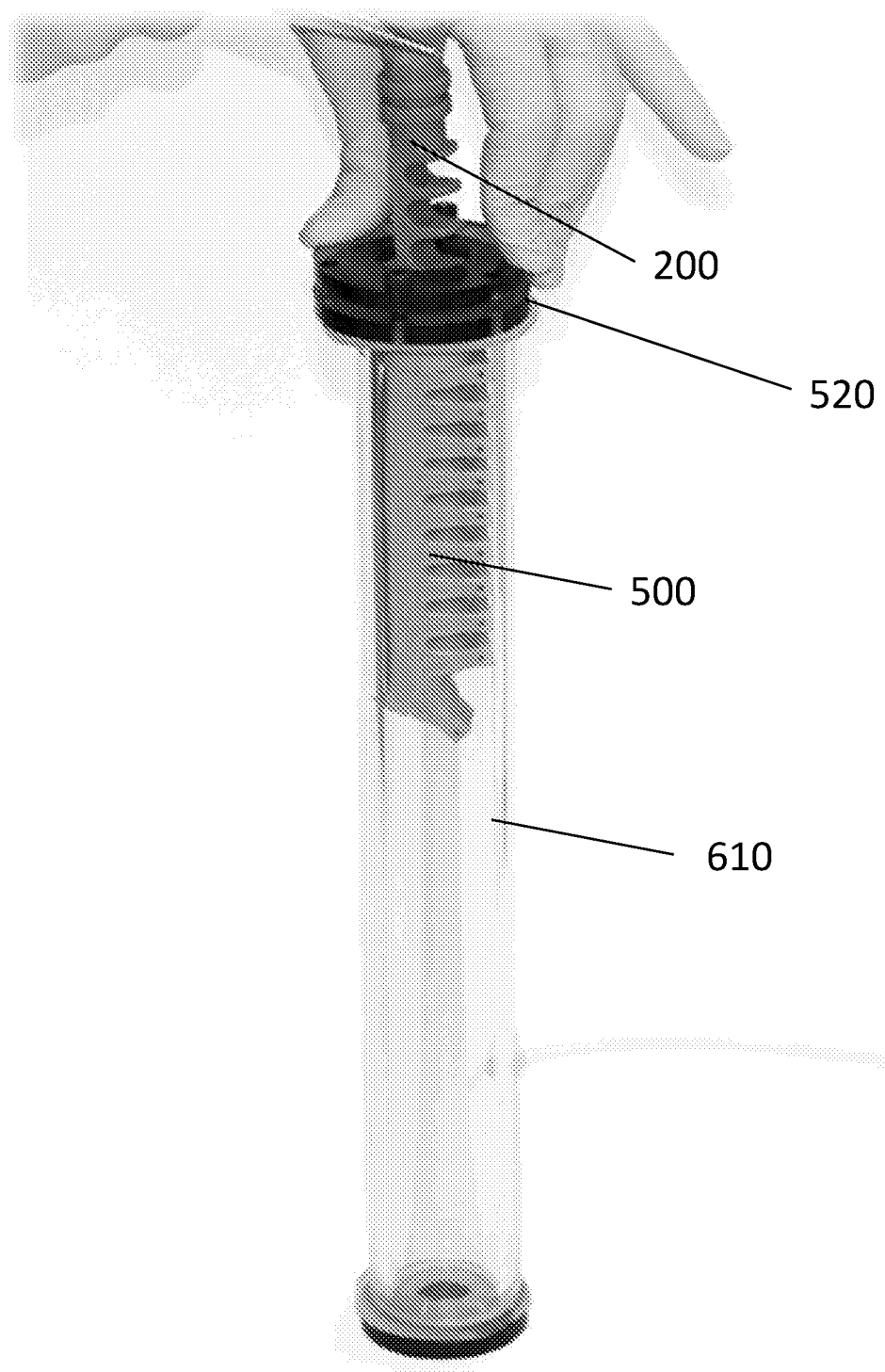
FIG. 6 is a photograph showing removal of the core from an expanded bellows actuator and the use of flange for sealing in a vacuum chamber, and applying vacuum to the exterior of the actuator while the interior is exposed to ambient.

In the seventh step, vacuum pressure is used to remove the core from the actuator body. Referring to FIG. 6, the molded actuator body 500 is inserted into a vacuum chamber 610. The flange 520 molded at the open end of the actuator body is used to create an air-tight seal with the open end of a tubular vacuum chamber. Core 200, being on the opposite side of the flange seal, is not in fluidic contact with the vacuum chamber. When vacuum is applied (e.g., see vacuum tube line used to evacuate the chamber interior) the actuator interior housing core 200 remains at atmospheric pressure, while the actuator's outer surface is subject to vacuum. This creates a pressure differential that expands and stabilizes the actuator body, allowing it to separate from core 200. The operator can pull out the core because the core retains its original size while the actuator expands. FIG. 6 is a photograph showing the removal of the core from the expanded bellows actuator chamber.

The core that defines the interior geometry of the actuator body can be made of rigid materials, soft materials, or any combination thereof. The selection of the core material depends in part on the stiffness of the material used to make the actuator body. For example, an actuator body made of soft material will expand considerably more than a stiffer material during the vacuum demolding step. Hence a rigid (or stiffer) core may be used in this step because the actuator body can inflate considerably out of the way to assist removal of the rigid core. An actuator body made of a stiffer material will not inflate as much, hence, a softer core is more desirable as its ability to deform can aid removable for complex interior bladder geometries.

Figure 7A:
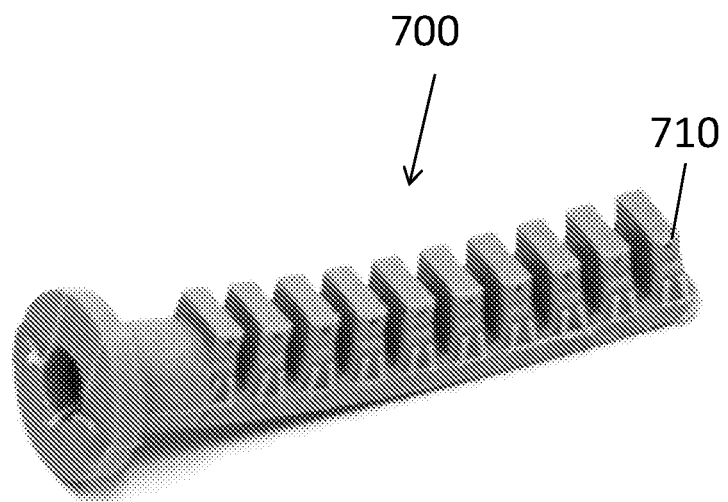
FIGS. 7A and 7B are various illustrations of the soft bellows actuator after removal of the core, according to one or more embodiments.
Figure 7B:
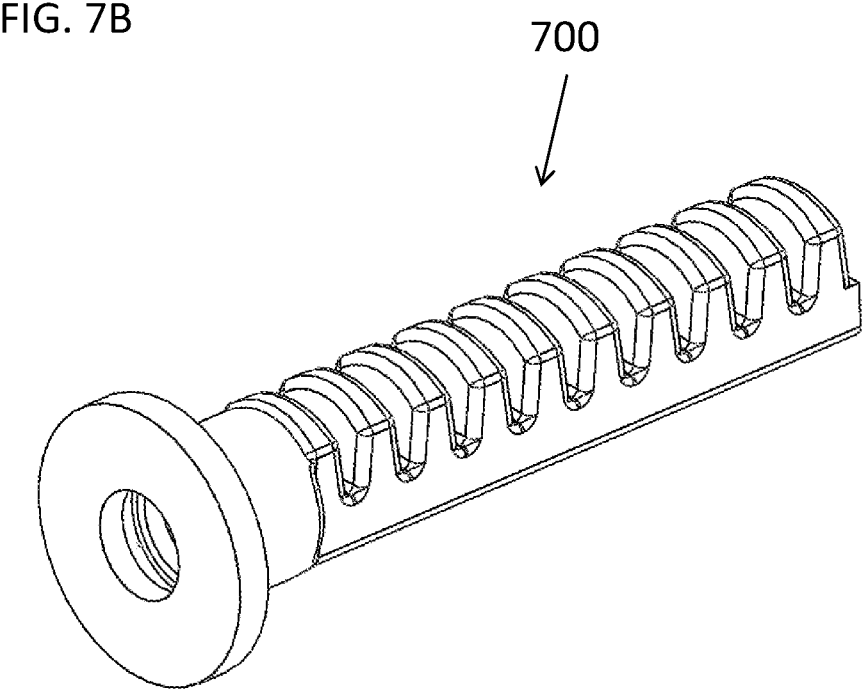

FIGS. 7A-7B are various illustrations of the soft bellows actuator 700 after removal of the core. The soft actuator includes through holes 710 that can be used to secure functional surfaces to the face of the actuator. The undamaged core (not shown), once removed from the actuator, is ready for reuse.

Figure 8A:
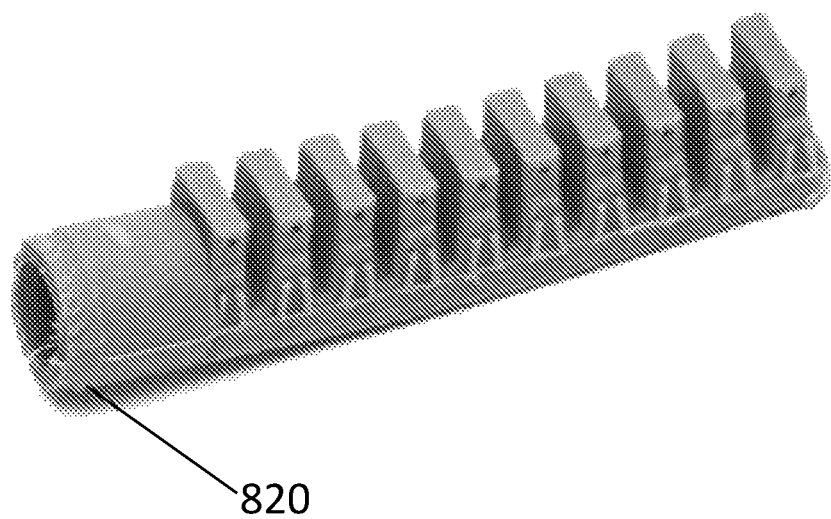
FIGS. 8A and 8B illustrate additional fabrication steps in the manufacture of a soft bellows actuator, according to one or more embodiments.
Figure 8B:
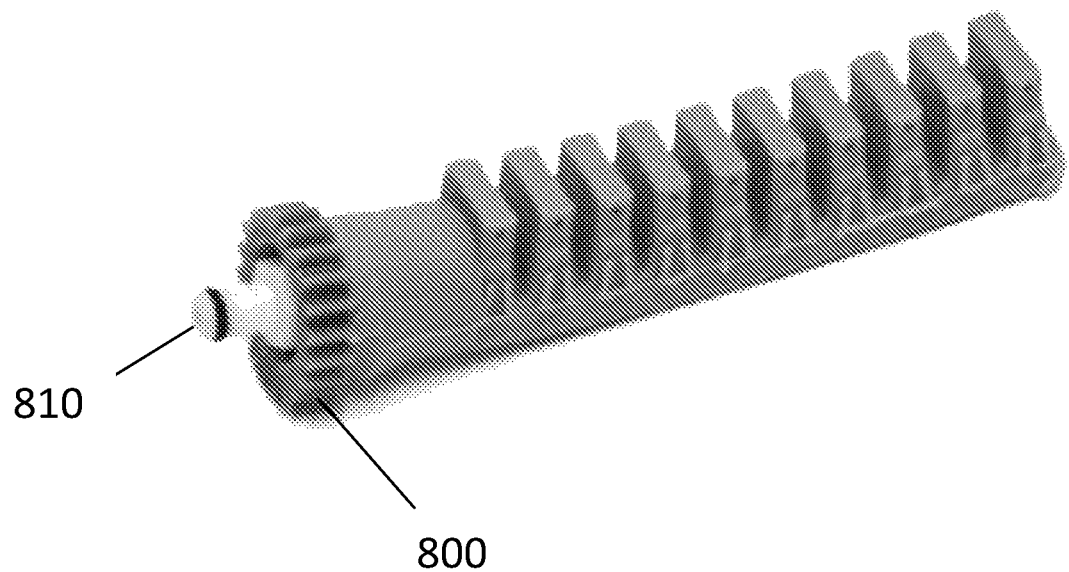

In the final assembly steps shown in FIGS. 8A-8B, the flange is cut off creating a collar 820, and a 3D printed fitting is glued into the open end. In one or more embodiments, the fitting features gear teeth 800 for integration with the robot base and integrated male quick disconnect 810 for easy actuator installation and removal. In other embodiments, if the flange is not cut off (as it is in FIG. 8A), it could be used to clamp the actuator body to a robot base.

Figure 9:
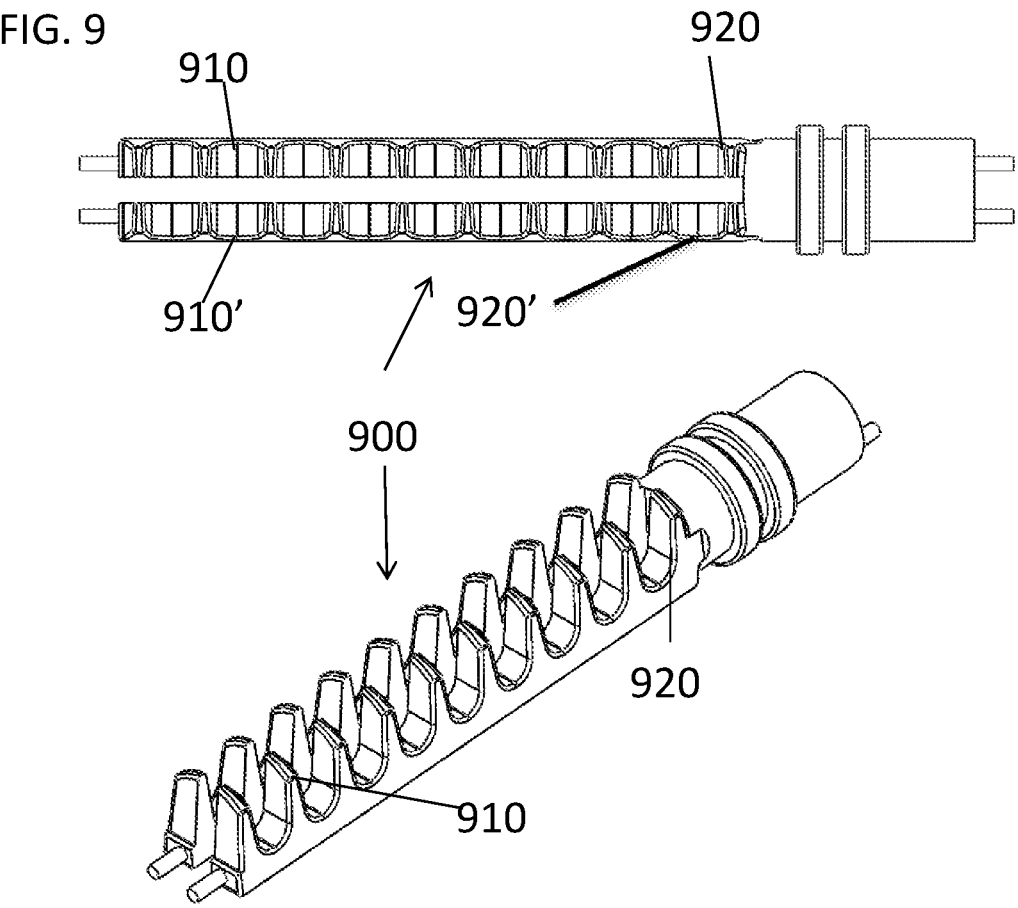
FIG. 9 shows top and perspective views of a core having two parallel, spaced apart branches with fins, according to one or more embodiments.

The use of reusable 'cores' and a vacuum technique for core removal enables the formation of complex interior shapes without damage on demolding. For example, the core can provide two parallel branches of fins. FIG. 9 shows a top and perspective view of a core 900 embodying these features. Each branch 910, 910' contains a set of fins 920, 920'. Other features of the core are as previously described.

Figure 10:
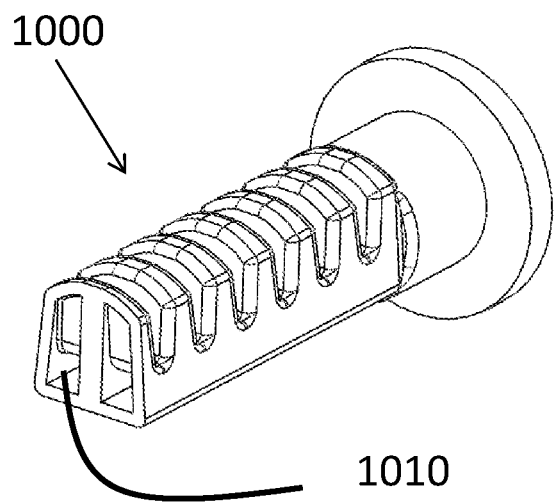
FIG. 10 shows the cross-section of an actuator body obtained using a core with two parallel branches according to one or more embodiments.
Figure 18A:
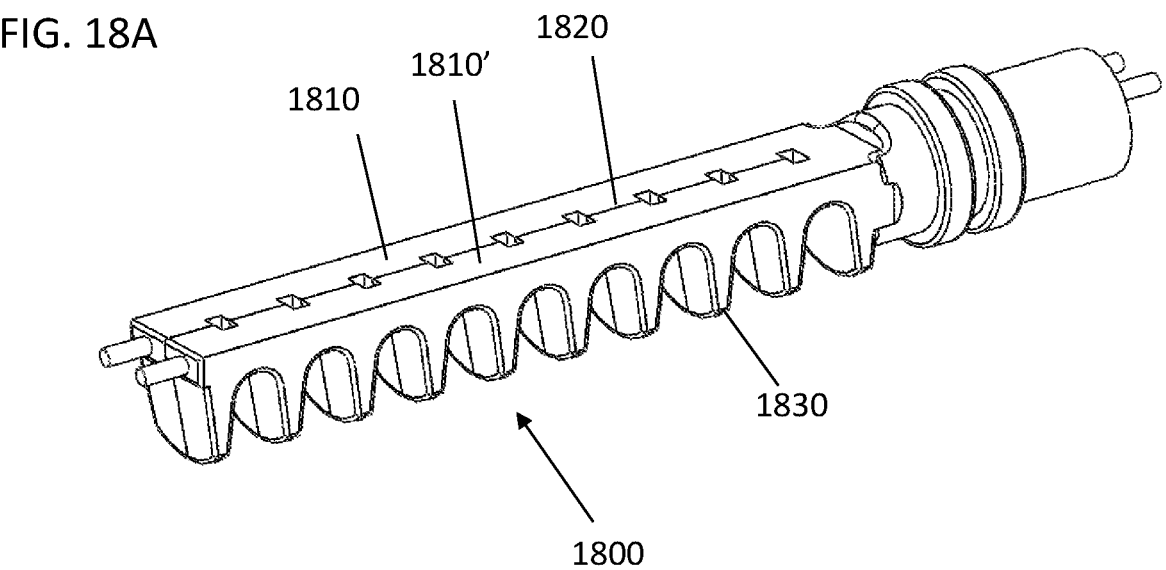
FIG. 18A shows a perspective view of a core having two parallel, adjacent branches with fins containing regularly spaced recesses, according to one or more embodiments.
Figure 18B:
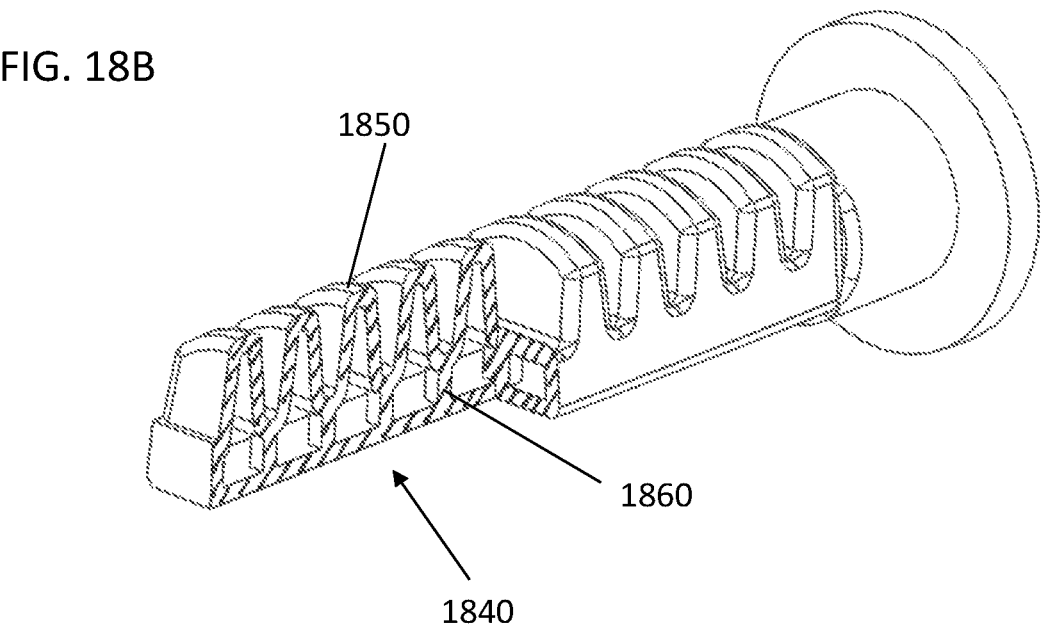
FIG. 18B is a schematic illustration (with partial cross sectional view) of an actuator body obtained using a core with two parallel branches in which the regularly spaced recesses of the mold are filled to create 'posts' or a raised base for each baffle fin, according to one or more embodiments. Note that a such an embodiment could be similarly obtained from a single unitary core having regularly spaced recesses.

A bellows actuator molded around such a core can contain a central interior rib that provides additional interior reinforcement that helps to minimize radial swelling. FIG. 10 shows a cross-section of an actuator body 1000 obtained using the branched core of FIG. 9. The space between the two parallel branches provides a central rib 1010 in the molded actuator. The rib provides an additional interior reinforcement to minimize radial swelling. In other embodiments, two parallel branches can be designed to create a plurality of reinforcing features such as periodic posts as opposed to a continuous rib. FIGS. 18A and 18B illustrate this embodiment. FIG. 18A is a schematic illustration of a core 1800 having two parallel branches 1810, 1810' that are positioned adjacent to one another at interface 1830 with regularly spaced openings 1830. FIG. 18B is an illustration of the molded actuator 1840 in partial cross-sectional view to show the interior. The adjacent branches result in connected fins 1850, each fin having its own base 1860.

Figure 17A:
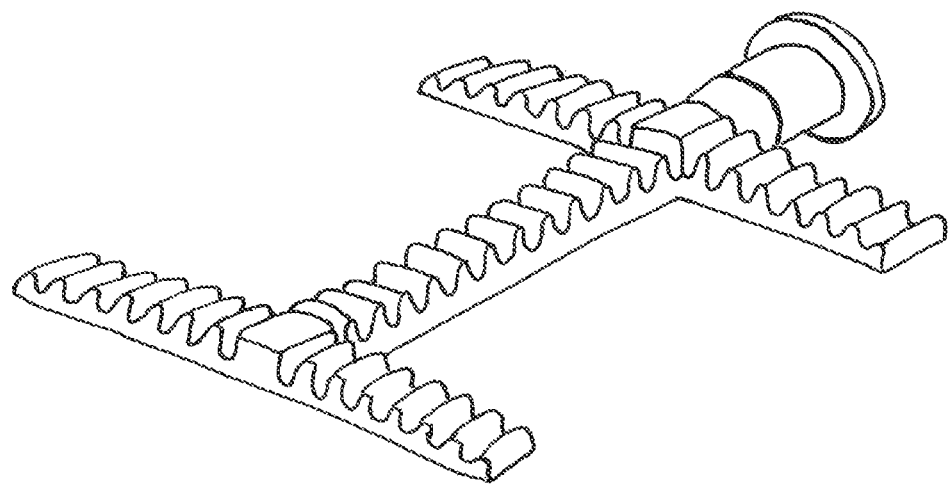
FIG. 17A is a schematic illustration of an actuator having multiple branching features that extend in various directions according to one or more embodiments.
Figure 17B:
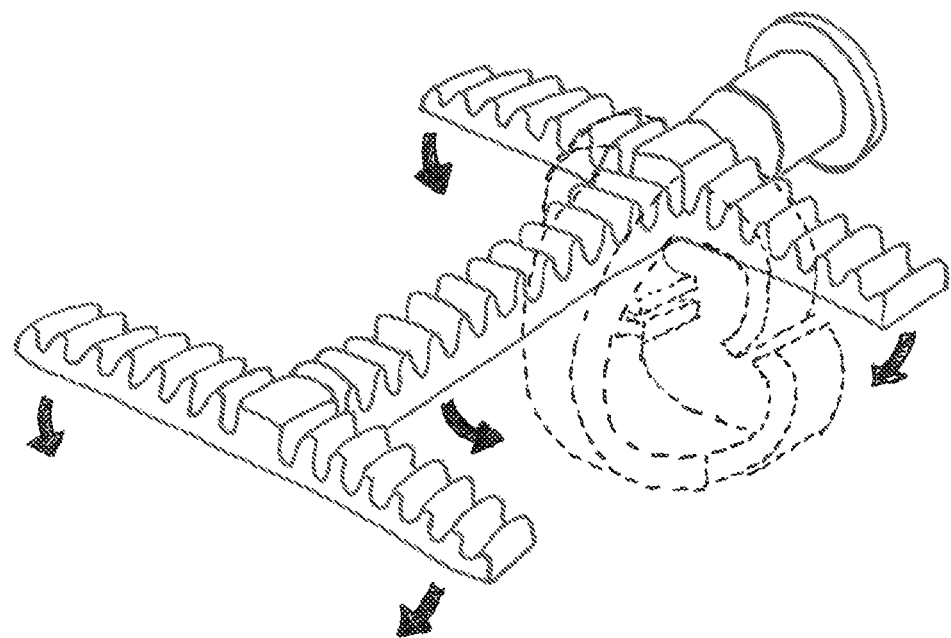
FIG. 17B shows the actuator motion when activated.

In other embodiments, the core can include multiple branching features that extend in different directions. In this manner, it is possible that a bellows actuator can undergo movements in more than one direction from a single input source. FIGS. 17A and 17B illustrate an embodiment of a bellow actuator having multiple branching features. Note that this design allows one pressurizing input to cause the actuator to execute a complex motion. However, it is contemplated that the actuator can be molded to allow for multiple inputs to, in effect, have multiple actuators within a single molded body.

Figure 11A:
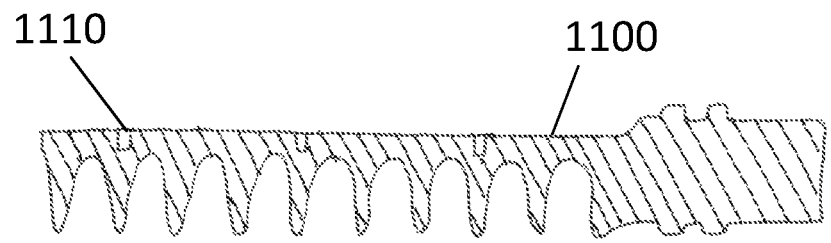
FIGS. 11A-11E are cross-sectional illustrations of a co-molding process that can be used to embed useful features in the bellows actuator according to one or more embodiments.
Figure 11B:
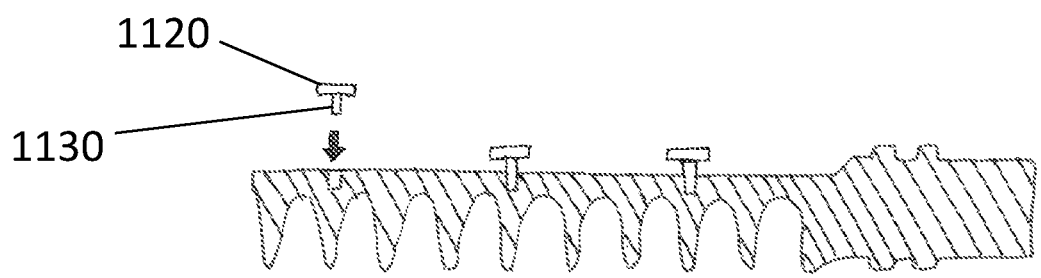
Figure 11C:
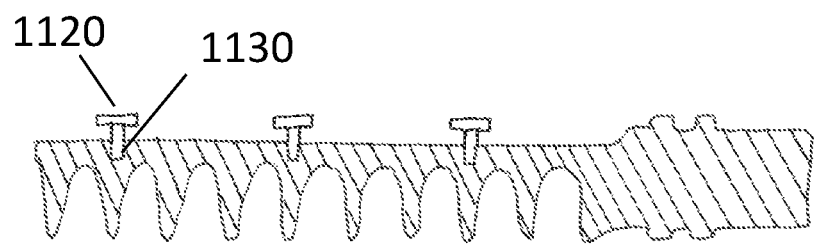
Figure 11D:
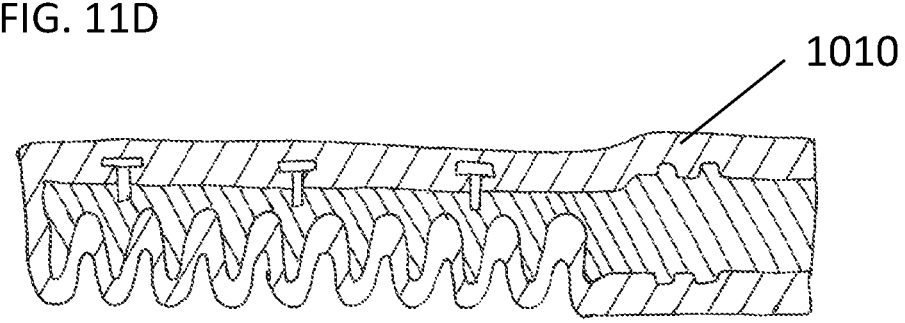
Figure 11E:
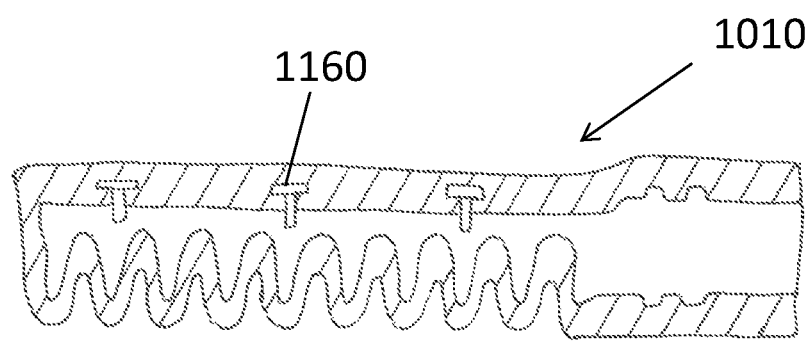

In other embodiments, the core can be fitted with features that are transferred into the bellows actuator on molding. The co-molding process is described with reference to FIGS. 11A-11E. In FIG. 11A, pocket 1110 are formed in core 1100. Features 1120 are then secured into the mold as shown in FIG. 11B. For example, features 1120 are mounted on posts 1130 that can be inserted into pockets 1110. The assembled core is shown in FIG. 11C. Next, the bellows actuator 1140 is molded around the core 1100, as shown in FIG. 11D. Core 1100 is removed as described herein and the features remain embedded in the walls of the actuator after the core is removed. An actuator having co-molded features 1160 is shown in FIG. 11E.

The features can be selected to perform several different functions in the actuator. The features can be selected from circuit boards, sensors, LEDs, batteries, magnetics markers, radiopaque markers, antennas, metal, plastic, composites, and the like in a co-molding process.

Figure 12:
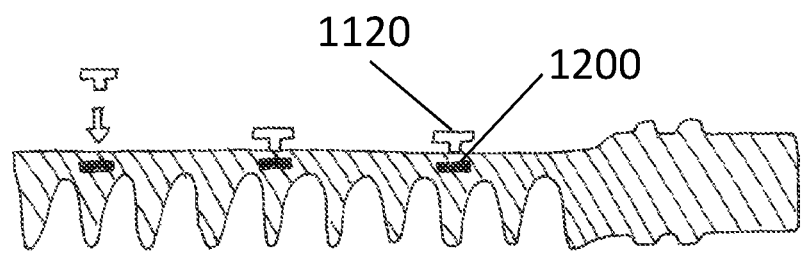
FIG. 12 is a cross-sectional illustration of a method for positioning features on a core according to one or more embodiments.

FIG. 12 illustrates another way in which the features 1120 can be positions on the mold. In an alternative embodiment, a magnet 1200 is embedded in the mold at locations were a feature 1120 is to be positioned. The features or post are magnetic or ferromagnetic and the magnetic attraction can be used to position or anchor the features.

Figure 13A:
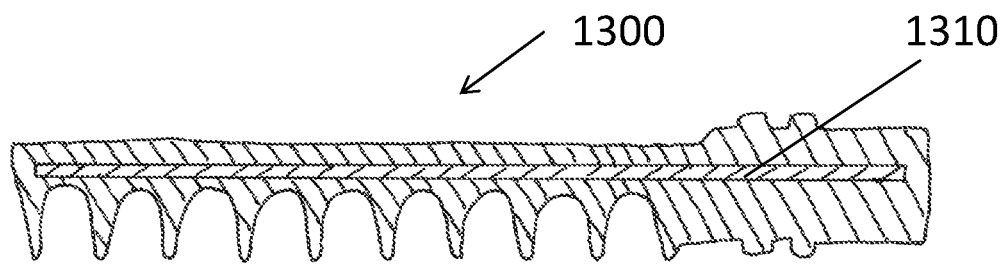
FIG. 13A is a cross-sectional view of a composite core having a strain limiting layer according to one or more embodiments.

In one or more embodiments, the core can be a composite core 1300, having a reinforcing material 1310, as shown in FIG. 13A. The material can be a strain limiting material, e.g., a woven material such as fiberglass, Kevlar aramid fabric, and the like, which helps to minimize the strain experienced by the rubber or other material used for the core. This is advantageous for repeated use of the core, so as not to fatigue the rubber leading to material failure.

Figure 13B:
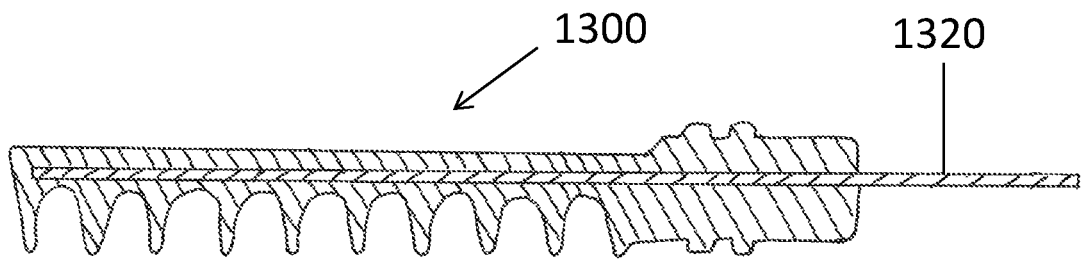
FIG. 13B is a cross-sectional view of a composite core having a stiff cantilevered insert according to one or more embodiments.

In other embodiments, the core can include a stiff insert 1320, as shown in FIG. 13B. The stiff insert can extend beyond the body of the core and provide a cantilever to be used during the molding step. The core can be cantilevered on a ledge adjacent the actuator mold, negating the need to employ rods that pierce the actuator walls.

Figure 14:
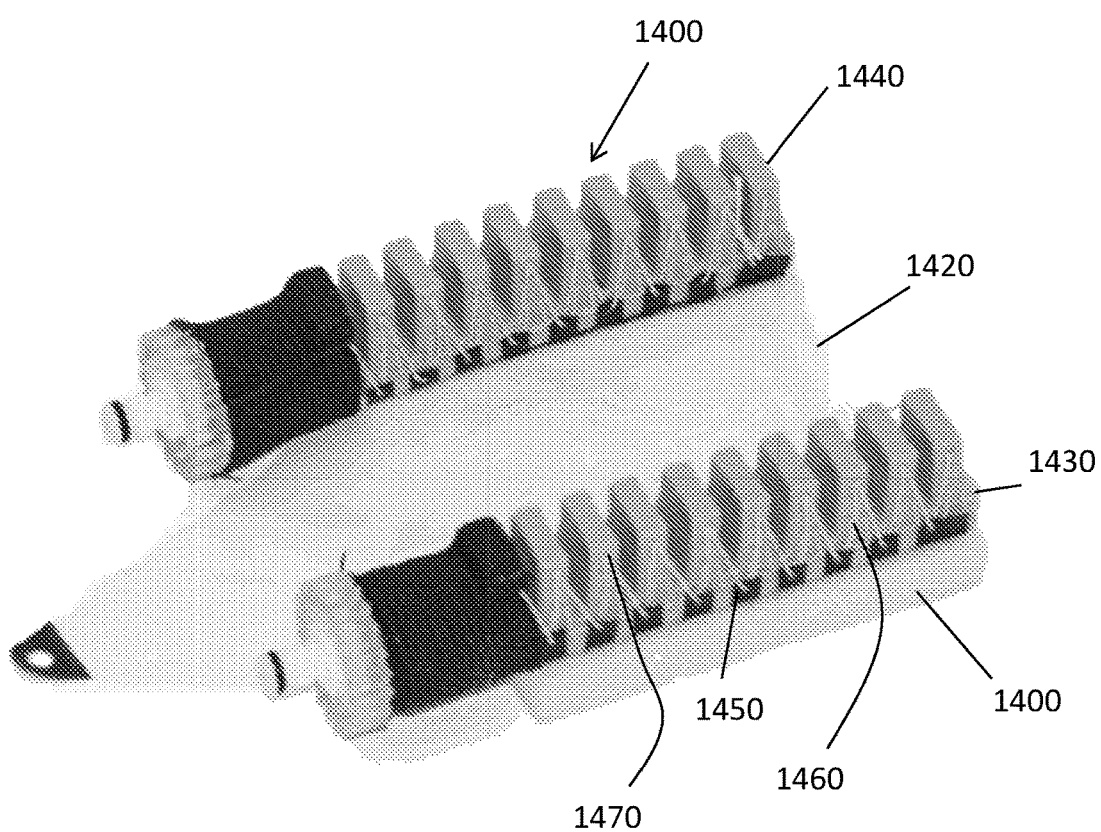
FIG. 14 is a photograph showing the attachment of a memory foam surface to the faces of a bellows actuator and a fabric attached and spanning adjacent bellows actuator, according to one or more embodiments.

In other embodiments, the actuator is capable of the addition and removal of textures and other accessories (e.g., netting material bridging the space between neighboring actuators) so that the capabilities of the actuators can be modified in the field. Referring to FIGS. 4 and 5, it is possible to introduce through holes 510 in the tips of the bellow fins by molding the actuator around rods 440 that extend across the width of the mold. The holes that are formed in the final product can be used to secure soft foam covers to render the actuator, which are softer and less likely to damage the gripped object. In other embodiments, a rough texture fabric can be applied to improve the gripping capability and reduce slippage. In other embodiments, a net or fabric can be extended between actuators to provide and actuatable net for collection of specimens. Other attachments are contemplated and non-limiting examples include rigid materials, knitted, woven and non-woven fabrics; and suction cups (active or passive). FIG. 14 is an illustration of one embodiment, illustrating the attachment of a soft foam cover 1400 and a fabric 1420 that spans between actuators 1430 and 1440. In this figure, attachment 1420 is comprised of TPU film (thermoplastic polyurethane) and fabric though it could be entirely fabric. The foam and/or fabric have tabs 1450 through which a string 1460 is passed. The string is threaded through holes 1470, in one side and out the other, where is passes through a tab on the far side and returns through as second through to the original side. The process is akin to 'sewing' the article (e.g., foam pad or fabric) to the actuator and has the advantage that is it secure during use, but readily disassembled.

In one or more embodiments, the actuator can be integrated into a robotic system having hardware and software to drive the robotic system. The functional requirements for the soft gripper design can be broadly categorized under two development topics: integration and operation. With respect to integration, the soft gripper hardware connects to existing robotic systems to drive the soft actuators. With respect to operation, the soft gripper is capable of quick soft actuator installation, adjustment (e.g., orientation and spacing), and removal.

Figure 15:
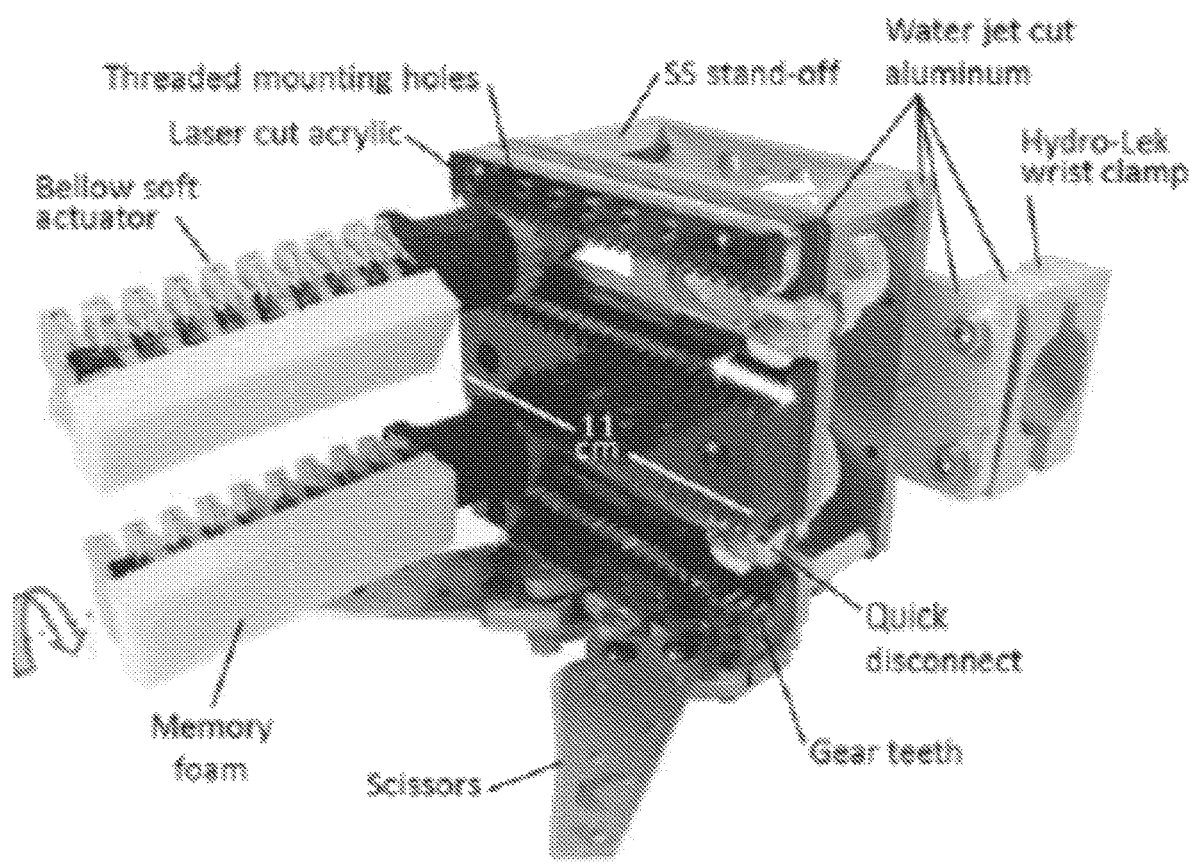
FIG. 15 is a photograph of an assembled soft robotic gripper featuring two bellows actuators with memory foam surfaces.

The soft gripper's palm is designed for rapid and inexpensive customization. An exemplary robot incorporating the ability to accommodate four actuators, as well as other tools, such as scissors, is shown in FIG. 15. The palm structure is assembled from sheet materials: water jet cut aluminum and laser cut acrylic. Four thru-wall female quick-disconnect fittings are positioned in recessed channels formed from stacked layers of acrylic. The relative spacing of the fittings can be manually adjusted. Furthermore, laser cut gear teeth in the acrylic sheets run parallel to the slots and match the 3D printed spur gear teeth integrated into the soft actuator base. When the gear teeth engage, this locks the position of the female quick-disconnect fitting and orientation of the soft actuator. Note that without the gear teeth, the actuator can passively rotate about the axis of the quick-disconnect fitting. The palm surface also features a variety of threaded holes that serve as anchor points for palm textures and other accessories. Stainless Steel (SS) threaded stand-offs create an open cavity between two aluminum plates for routing hydraulic plumbing to the female quick-disconnects. These plates also serve as anchor points for a bowden-cable driven, four-bar linkage cutting mechanism. Custom fittings were machined to connect the Hydro-Lek arm's push-pull rod to the cutter. Vented screws terminate each end of the Bowden cable sheath and are tightened or loosened to tension the cable. Cutting blades are screw mounted to one of the linkages enabling replacement with and evaluation of new blade designs.

The operation and gripping of the soft robot is shown in FIGS. 16A-16D. FIGS. 16A and 16B provide isometric and top views, respectively, of the bellows-type soft actuators under vacuum in the open pose state. FIGS. 16C and 16D provide isometric and top views, respectively, of the bellows-type soft actuators pressurized to 124 kPa (18 psi).

The performance of the bellows actuators was evaluated to understand the magnitude of the force and pressure applied to static objects. A 63.5 mm diameter plastic tube was selected as the target object because both soft actuator types could cradle more than half the circumference of the tube and the radius of curvature was suitable for wrapping around a Tekscan (model: 5051-20) pressure mapping sheet. The bellow-type actuators (pressurized to 69 kPa (10 psi)) demonstrated maximum pressures of 2 kPa (0.29 psi) and 7 kPa (1 psi), with and without foam, respectively.

The soft actuators grip strength was evaluated with a materials characterization system (Instron, model: 5544A single column) to analyze load-extension characteristics for several gripper scenarios including load direction (i.e., vertical vs. horizontal) and object size. In the experimental protocol, an acrylic tube ranging in diameter from 12.7, 25.4, and 50.8 mm was positioned at the palm of the gripper, and the actuators were inflated to their target pressures enclosing the cylinder. All bellows-type actuators were pressurized to 124 kPa (18 psi). Furthermore, the grip strengths of the bellows-type actuators were evaluated with only two actuators one opposing the other. The gripper was anchored to the table, and the Instron pulled on the tube at a fixed velocity (8 mm/s) until the cylinder was pulled from the actuator's grasp. Each test configuration was conducted five times and averaged. While gripping the 50.8 mm diameter tube, the bellows-type actuator had the greatest resistive force in the vertical direction (16.6 N), but offered relatively little resistive force in the horizontal direction (5.6 N).

Unless otherwise defined, used, or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments. Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise.

It will be appreciated that while a particular sequence of steps has been shown and described for purposes of explanation, the sequence may be varied in certain respects, or the steps may be combined, while still obtaining the desired configuration. Additionally, modifications to the disclosed embodiment and the invention as claimed are possible and within the scope of this disclosed invention.

The invention claimed is:

1. A method of making an actuator having a complex internal shape, comprising:
   providing a core of a shape that defines an internal cavity of an actuator;
   molding an actuator around the core, wherein the core occupies the internal cavity of the actuator, the cavity having an opening;

generating a pressure differential between an exterior surface of the molded actuator and the internal cavity of the actuator by fluidically isolating the exterior surface of the actuator from the internal cavity and applying a vacuum to the actuator, wherein the external pressure is less than the internal pressure, to expand the actuator cavity; and removing the core through the opening of the expanded actuator cavity.

2. The method of claim 1, wherein the core is reusable.

3. The method of claim 1, wherein the core is made of a lower durometer material than the molded actuator.

4. The method of claim 1, wherein fluidically isolating the actuator comprises introducing the molded actuator into a chamber and forming a seal between the cavity opening and the chamber so that the cavity is external to the chamber.

5. The method of claim 4, wherein the molded actuator comprises a flange around the cavity opening and the seal is created between the flange and the chamber.

6. The method of claim 1, wherein the core comprises fins and defines the internal cavity shape of a bellows.

7. The method of claim 6 wherein molding an actuator around the core comprises positioning the core in a mold, said mold defining the external shape of a bellows actuator.

8. The method of claim 7, wherein molding the bellows actuator further comprises molding through holes through a tip of the bellows.

9. The method of claim 8 wherein molding through holes through a tip of the bellows comprises positioning a pin transversely across the bellows mold in a location defining the tip or the bellows.

10. The method of claim 6, wherein the fins have a high aspect ratio.

11. The method of claim 1, wherein the core comprises a plurality of branches.

12. The method of claim 11, wherein the plurality of branches is in parallel.

13. The method of claim 11, wherein the plurality of branches is positioned in different directions.

14. The method of claim 1, wherein the actuator is molded around a plurality of cores, each core defining a cavity having an opening.

15. The method of claim 1, wherein the core comprises a composite core.

16. The method of claim 15, wherein the composite core comprises a reinforcing member.

17. The method of claim 16, wherein the reinforcing member is a strain limiting member, a strengthening member or a cantilevered member, a fiber reinforcement, or combinations thereof.

18. The method of claim 1, further comprising co-molding an attachment with the actuator by securing the attachment on a surface of the core before molding the actuator around the core.

19. The method of claim 1, further including fastening a valve connection in the open cavity for use in connecting the actuator to a pressurizing source.

20. A bellow actuator, comprising:
a flexible molded body comprising an actuator interior, said flexible molded body having a flat base and an upper surface molded to define a plurality of fins, each fin integral to the base and at least partially separated from adjacent fins, wherein each fin comprises a fin tip and the fin tips comprise through holes, said through holes in fluidic isolation from the actuator interior and
an attachment secured to the flat base by a string that is thread through the plurality of through holes.

21. The bellow actuator of claim 20, wherein the attachment is selected from the group of cushioning material, memory foam, high friction material, rigid materials, knitted, woven and non-woven fabrics, and suction cups (active or passive).

22. The bellow actuator of claim 20, wherein the actuator is closed at one end and open at the opposite end and the open end is fitted with a valve for connection to a pressurizing source.

23. The bellow actuator of claim 22, wherein the open end further comprises gear teeth for meshing with a robot base.

24. The bellow actuator of claim 20, wherein the flat base comprises through holes, said through holes in fluidic isolation from the actuator interior.

25. The bellow actuator of claim 20, wherein the actuator comprises an integrally molded support post extending from the base to fin tip.

26. The bellow actuator of claim 20, wherein the actuator comprises an integrally molded support post spanning the base and upper mold surface at a location between adjacent fins.

27. A soft robotic gripper comprising:
a plurality of bellow actuators according to claim 20, said bellow actuators secured to a base and positioned to bend towards one another on pressurization.

* * * * *